(12) United States Patent
Bamberger et al.

(10) Patent No.: US 7,289,650 B2
(45) Date of Patent: Oct. 30, 2007

(54) WORKSTATION FOR COMPUTERIZED ANALYSIS IN MAMMOGRAPHY

(75) Inventors: Philippe Nathan Bamberger, Jerusalem (IL); Isaac Leichter, Jerusalem (IL); Nicolas J. Merlet, Jerusalem (IL)

(73) Assignee: Siemens Computer Aided Disgnosis Ltd., Jerusalem (IL)

( * ) Notice: Subject to any disclaimer, the term of this patent is extended or adjusted under 35 U.S.C. 154(b) by 751 days.

(21) Appl. No.: 10/722,289

(22) Filed: Nov. 25, 2003

(65) Prior Publication Data

US 2004/0165792 A1  Aug. 26, 2004

(30) Foreign Application Priority Data

Nov. 28, 2002  (IL) ..................... 153162

(51) Int. Cl.
*G06K 9/00* (2006.01)
(52) U.S. Cl. .................. 382/128; 382/305; 378/37
(58) Field of Classification Search ............. 382/128, 382/129, 130, 131, 132, 168, 175, 180, 260, 382/274, 318, 181, 254, 133, 173, 232–243, 382/276, 305; 250/580; 270/58.31; 707/201; 358/1.12; 378/21, 37
See application file for complete search history.

(56) References Cited

U.S. PATENT DOCUMENTS

| | | | | |
|---|---|---|---|---|
| 5,729,620 A | 3/1998 | Wang | .................. | 382/128 |
| 5,815,591 A | 9/1998 | Roehrig et al. | ............. | 382/130 |
| 5,828,774 A | 10/1998 | Wang | .................. | 382/128 |
| 5,854,851 A | 12/1998 | Bamberger et al. | ........ | 382/132 |
| 5,886,359 A * | 3/1999 | Bringley et al. | ............ | 250/580 |
| 5,953,500 A * | 9/1999 | Katakura | .................. | 358/1.12 |
| 5,970,164 A | 10/1999 | Bamberger et al. | ........ | 382/128 |
| 6,075,879 A | 6/2000 | Roehrig et al. | ............. | 382/132 |
| 6,198,838 B1 | 3/2001 | Roehrig et al. | ............. | 382/132 |
| 6,227,531 B1 * | 5/2001 | Guerrero et al. | ......... | 270/58.31 |
| 6,266,435 B1 | 7/2001 | Wang | .................. | 382/132 |
| 6,434,262 B2 * | 8/2002 | Wang | .................. | 382/132 |
| 6,678,703 B2 * | 1/2004 | Rothschild et al. | ......... | 707/201 |
| 7,146,031 B1 * | 12/2006 | Hartman et al. | ........... | 382/132 |

* cited by examiner

*Primary Examiner*—Azarian Seyed

(57) ABSTRACT

A method of separating and collating mammogram records, the method including the step of providing and scanning a separator film having identifiable features which when scanned identify the film as a separator film, thereby assisting in the separation of mammograms of different patients. A separator film for use with a mammogram workstation the film having at least one identifiable characteristic recognizable by the workstation's processing means so that the film is identified as a separator film separating mammograms of different patients. A workstation system for collating radiological film mammograms which includes a scanner which digitizes radiological film mammograms and scans a separator film carrying identifiable features for identifying the film as a separator film usable to separate mammograms of different patients.

17 Claims, 7 Drawing Sheets

WORKSTATION FOR COMPUTERIZED ANALYSIS IN MAMMOGRAPHY

FIELD OF THE INVENTION

The present invention relates to a mammogram workstation and a method for using such a workstation.

BACKGROUND OF THE INVENTION

Breast cancer is one of the most common types of cancer afflicting Western society. It is estimated that the spread of the disease has risen in the United States, from one in twenty women being afflicted in 1940, to one in eight in 1995. The American Cancer Society estimated that 183,000 new cases of breast cancer were reported during 1995. In the United States, some 46,000 women die from the disease per year. Today, it is accepted that the best way to detect breast cancer in its early stages is by annual mammography screening of women aged 40 and up.

Today, radiologists generally interpret mammograms visually, using a light box, and their analysis is largely subjective. Film masking is used to highlight additional detail. In many cases, the radiologist employs supplementary tools such as a magnifying glass and bright light sources to evaluate very dark regions. If the mammogram is not conclusive the radiologist must recall the patient for an additional mammogram using one or more of the following techniques:

1. adding a view with a different projection;
2. performing a magnification mammogram by changing the distance between the breast and the film;
3. locally compressing the breast in the area of suspected abnormality;

The analysis, even after using the above techniques, still remains mainly subjective.

In order to aid radiologists in reducing the false negative rate in mammographic screening, computer systems using specialized software and/or specialized hardware have been developed. These systems, often called computer-aided detection systems, hereinafter often denoted as "CAD systems", have been known for many years and have been reported extensively. As noted below, their use in evaluating mammograms has been discussed at length in both the patent and professional literature.

CAD systems are typically used as follows. A radiological technician or a radiologist takes a set of radiological film images of the patient following a predetermined protocol. A radiologist views the film images and reaches a preliminary diagnosis. The radiologist next views separate, second images that are generated by the CAD system after processing the scanned and digitized set of film images. Typically, suspected abnormalities detected by the CAD system through computer analysis of the digitized version of the respective radiological film images appear as marked locations on the second images. After a reexamination of the areas of the original film images that correspond to the positions of the suspected abnormalities displayed on the CAD system, the physician makes a final diagnosis and determines a course of further action.

FIG. 1 to which reference is now made shows a block diagram of a simplified prior art CAD system designated as 100. Radiological films 110 taken by a radiologist or technician are scanned into and digitized by a digitizer 114. The digitized image produced is then fed into a processor 142, which uses any of many known algorithms to detect suspected abnormalities on the mammogram. Typical algorithms used for detecting abnormalities on the mammogram can be found in many of the references cited below. The digitized image is displayed on display 134. The displayed image shows the abnormalities detected, a location marker typically marking each abnormality. The image can be manipulated through a keyboard or other input device. Using a keyboard 138, the user instructs the processor to send the displayed images to a printer 118 for printing. The printout of the displayed digitized images includes location markers indicating suspected abnormalities on the images.

Computer-aided detection (CAD) mammography systems, and algorithms for use therewith, have been discussed extensively in many issued patents. An overview of the field can be obtained by reviewing U.S. Pat. Nos. 5,729,620 (Wang); 5,815,591 (Roehrig et al); 5,828,774 (Wang); 5,854,851 (Bamberger et al); 5,970,164 (Bamberger et al); 6,075,879 (Roehrig et al); 6,198,838 (Roehrig et al); 6,266,435 (Wang); and 6,434,262 (Wang). These patents, including references cited therein, are hereby incorporated by reference in this specification as though fully set forth herein.

Generally, a radiologist reads and analyzes several sets of mammograms one after another, each set relating to a different patient. The radiological films of the patients are often commingled during the digitizing process, as are the printed reports generated by the printer. Significant time is required by the staff of a radiology department to sort and collate the films with their respective printouts for insertion into the patient's physical files. The commingling of film and printed reports allows for the possibility of misplacement, error or even loss. In addition, the separation of films and printed reports, and then their subsequent collation generally requires a large work area.

While many prior art patents discuss collation of medical records, to the best of the inventors' knowledge they almost always pertain to collating digital records and do not relate to the collation of physical records. Typical, prior art medical data management and collating systems and methods can be found, for example, in U.S. Pat. Nos. 6,272,481 (Lawrence et al); 6,336,903 (Bardy); and 6,368,284 (Bardy). All appear to be computer-based systems and methods dealing with digital records, and they do not provide for collating and filing physical records.

In the case of mammograms the retention and organization of the physical radiological films is mandated. A workstation and method for retaining, organizing and assisting in the filing of radiological film mammograms together with related digitally produced printouts is required but lacking. Such a workstation and method would require less time for data management and would prevent errors.

SUMMARY OF THE PRESENT INVENTION

It is an object of the present invention to provide a system and method for collating radiological films and their associated physical data generated during mammogram screening.

It is a further object of the present invention to provide a method and a system for collating mammogram films and printouts that is useful in both large and small environments, e.g. hospitals and radiological clinics.

An additional object of the present invention is to provide a system and method for collating and filing mammogram films and data that can be carried out in smaller work areas.

Today collating and filing requires relatively large areas to collate and file the physical records produced by mammogram screening.

An additional objective of the present invention is to provide a mammogram display having a pre-selected order for the displayed digitized images, irrespective of the order in which the film mammograms have been fed into the scanner.

A further objective of the present invention is to provide a method for automatically isolating, that is separating, the digitized images generated from analog film mammograms of one patient from another. Additionally, it is an object of the invention to keep the film mammograms and their associated physical data, e.g. digitized image printouts, of one patient physically separate from those of another. This separation simplifies filing the mammograms in physical storage containers. Both of these separation objectives are achieved with separator films described in the present invention.

There is thus provided in accordance with the present invention a method of separating and collating mammogram records, the method including the steps of: scanning one or more radiological film mammograms relating to a patient thereby obtaining one or more digitized images; storing the one or more digitized images in a memory; providing and scanning a separator film having identifiable features which when scanned identify the film as a separator film, and positioning the separator film immediately after the one or more radiological films of a patient; and repeating the scanning, storing and providing steps for all remaining film mammograms of all patients in a film mammogram queue. The digitized images generated subsequent to each scanned separator film are stored separately from the stored digitized images obtained from prior scanned film mammograms.

In yet another embodiment of the invention, the method further includes a printing step, the printing step providing a printout of the one or more digitized images of the one or more film mammograms of a patient. The printing step also includes conveying and positioning the printout together with the one or more film mammograms. The one or more film mammograms and printout form a collated package of physical data relating to a single patient. Generally, the printout contains location markers indicating anatomical abnormalities found on each mammogram. Sometimes the printing step is effected prior to the providing step, more often the printing step is effected after the separator film has been scanned and identified as a separator film. When a printing step is included, it is also repeated in the above mentioned repeating step In yet another embodiment of the invention, the method includes an inputting step where patient identifier data are entered. Sometimes the inputting step is effected prior to the providing step as discussed previously. More often the inputting step is effected prior to the scanning step. When an inputting step is included, it is also repeated in the above mentioned repeating step.

In other embodiments of the invention, the step of inputting enters identifier data for every patient having a set of mammograms in the mammogram queue before any scanning begins and the repeating step includes repeating only the scanning, storing, providing, and printing steps.

In another aspect of the present invention there is provided a method for separating and collating mammogram records, the method includes the steps of: scanning a set of film mammograms relating to a patient thereby to obtain at least one digitized image of the set of film mammograms; moving the scanned set of mammograms to a collating station; providing and scanning a separator film, and positioning the separator film immediately after the at least one radiological film of a patient; positioning the separator film so that it is the last film of the scanned set of film mammograms located at the collating station; repeating the scanning, moving, providing and positioning steps for all N sets of film mammograms in a film mammogram queue, where N≧1; and transferring each of the N sets of film mammograms positioned between separator films to its own individual storage container for storage.

In another preferred embodiment of this aspect of the invention, the method further includes: a printing step, the printing step providing a printout of the at least one digitized image; and a conveying step, the conveying step conveying and positioning the printout together with the set of film mammograms at the collating station, whereby the set of film mammograms and printout form a collated package of physical data relating to a single patient. Generally, the printout generated by the printing step contains location markers indicating anatomical abnormalities found on each mammogram. Sometime the printing and conveying steps are effected prior to the providing step, but more often the printing and conveying steps are effected prior to the positioning step. When printing and conveying steps are included, they are also repeated in the repeating step.

In yet another embodiment of this aspect of the invention, the method may further include an inputting step wherein patient identifier data are entered. Sometimes the inputting step is effected prior to the providing step while more often times the inputting step is effected prior to the scanning step. When an inputting step is included, it is also repeated in the repeating step. More often when there is an inputting step, the inputted identifier data for every patient having a set of mammograms in the mammogram queue is entered prior to beginning the scanning step and the repeating step includes only the scanning, moving, providing, positioning, printing and conveying steps.

In yet another aspect of the invention, there is provided a method for displaying digitized images of film mammograms on the display of a mammogram workstation, where the method includes the steps of: scanning a set of radiological film mammograms relating to a patient, thereby to obtain digitized images of the set of film mammograms; storing the digitized images in a memory; analyzing the digitized images to determine the view of each digitized image; and using the determined views of each image to display the digitized images in a pre-selected order irrespective of the order in which the film mammograms were scanned.

There is provided in accordance with another aspect of the present invention a workstation system for collating radiological film mammograms and other physical records. The system includes a scanner which receives and digitizes radiological film mammograms of a patient and a separator film carrying identifiable features for identifying the film as a separator film. It also includes a collating station for receiving the scanned films from the scanner. The system has a processing means for receiving digitized images from the scanner. The processing means is operative to evaluate the digitized images of the film mammograms so as to detect suspicious lesions. It also generates output data indicative of such lesions, the data being stored in association with the digitized images. The processing means is further operative to detect the scanned separator film and to assign all subsequent scanned radiographic film mammograms to other patients. The system further includes a printer in communication with the processing means for producing a printout of the digitized images, identifying data, and output data relating to the patient. The printer includes a conveyor for conveying the printout to the collating station. Finally, the system contains a means for synchronizing the scanner and the printer so that the printout is laid on the scanned films prior to the delivery of the separator film to the collating station.

Additionally, in accordance with a preferred embodiment of the present invention, the system further includes a display for displaying the digitized images of scanned radiological film mammograms received from the processing means which is in electronic communication with the display.

Additionally, in accordance with a preferred embodiment of the present invention, the processing means of the system operates the display so that the digitized images are displayed in a pre-selected order irrespective of the order in which the film mammograms were scanned by the scanner.

In yet another embodiment of the invention, the system further includes an input device for entering identifier data relating to the patient.

In some embodiments of the invention the conveyor includes a set of rollers, while in others, the conveyor is a paper guide.

There is provided in accordance with another aspect of the present invention a separator film for use with a mammogram workstation where the workstation includes a scanner and a processing means. The film has one or more identifiable characteristics recognizable by the processing means which determine that the film is a separator film. The determination of the film as a separator film indicates to the processing means that all subsequently scanned film mammograms relate to patients other than patients whose film mammograms were scanned prior to the separator film. In another embodiment of the separator film, the separator film is for use with any of the embodiments of the workstation system described above.

In another embodiment of the present invention, the one or more identifiable characteristics are chosen from among the following: graphical indicia; a marker; a textured edge, and a serrated edge.

BRIEF DESCRIPTION OF THE DRAWINGS

The present invention will be understood and appreciated more fully from the following detailed description taken in conjunction with the drawings in which.

Similar elements in the Figures are numbered with similar reference numerals.

DETAILED DESCRIPTION OF PREFERRED EMBODIMENTS

Figure 1:
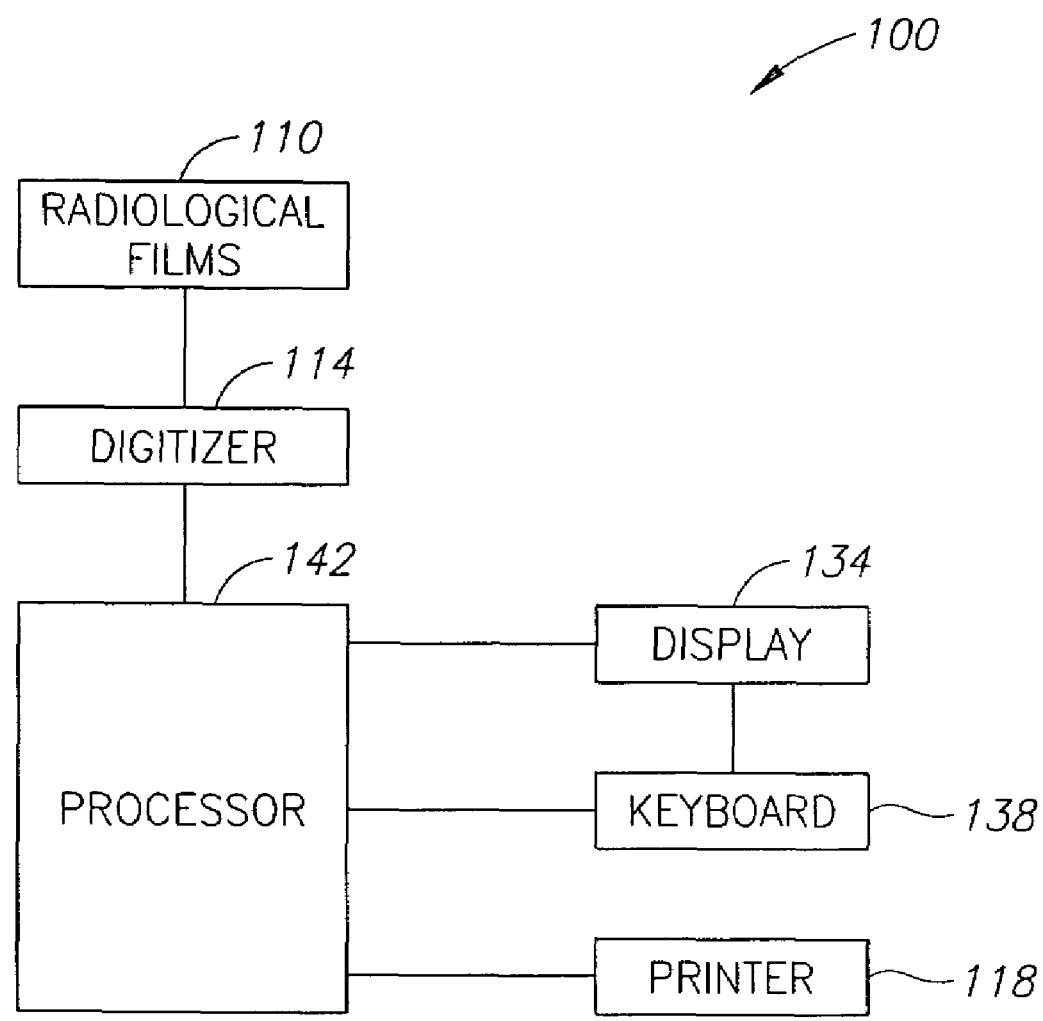
FIG. 1 is a block diagram of a prior art CAD system.
Figure 2A:
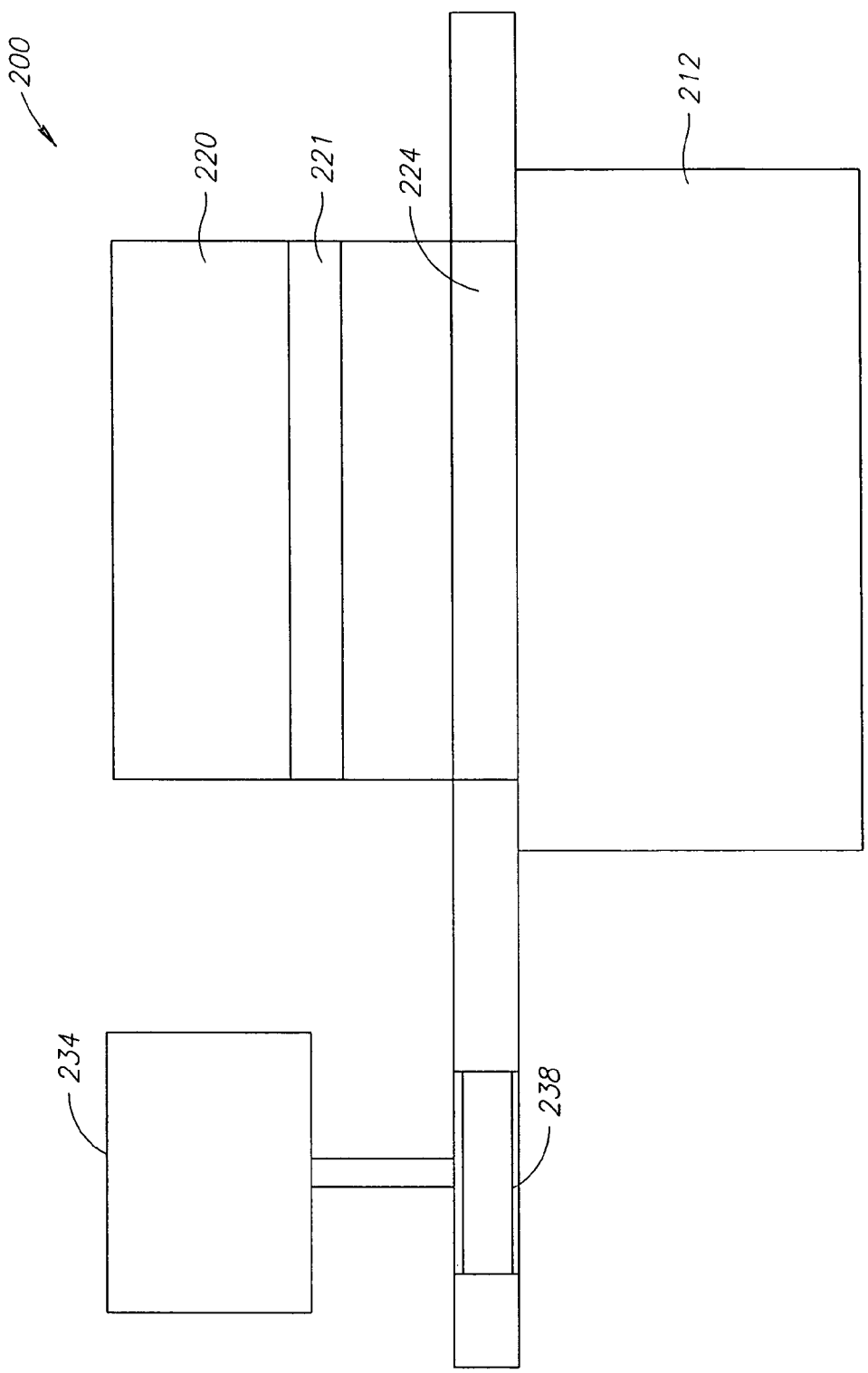
FIGS. 2A-2C are three schematic views of a mammogram workstation constructed in accordance with an embodiment of the present invention.
Figure 2B:
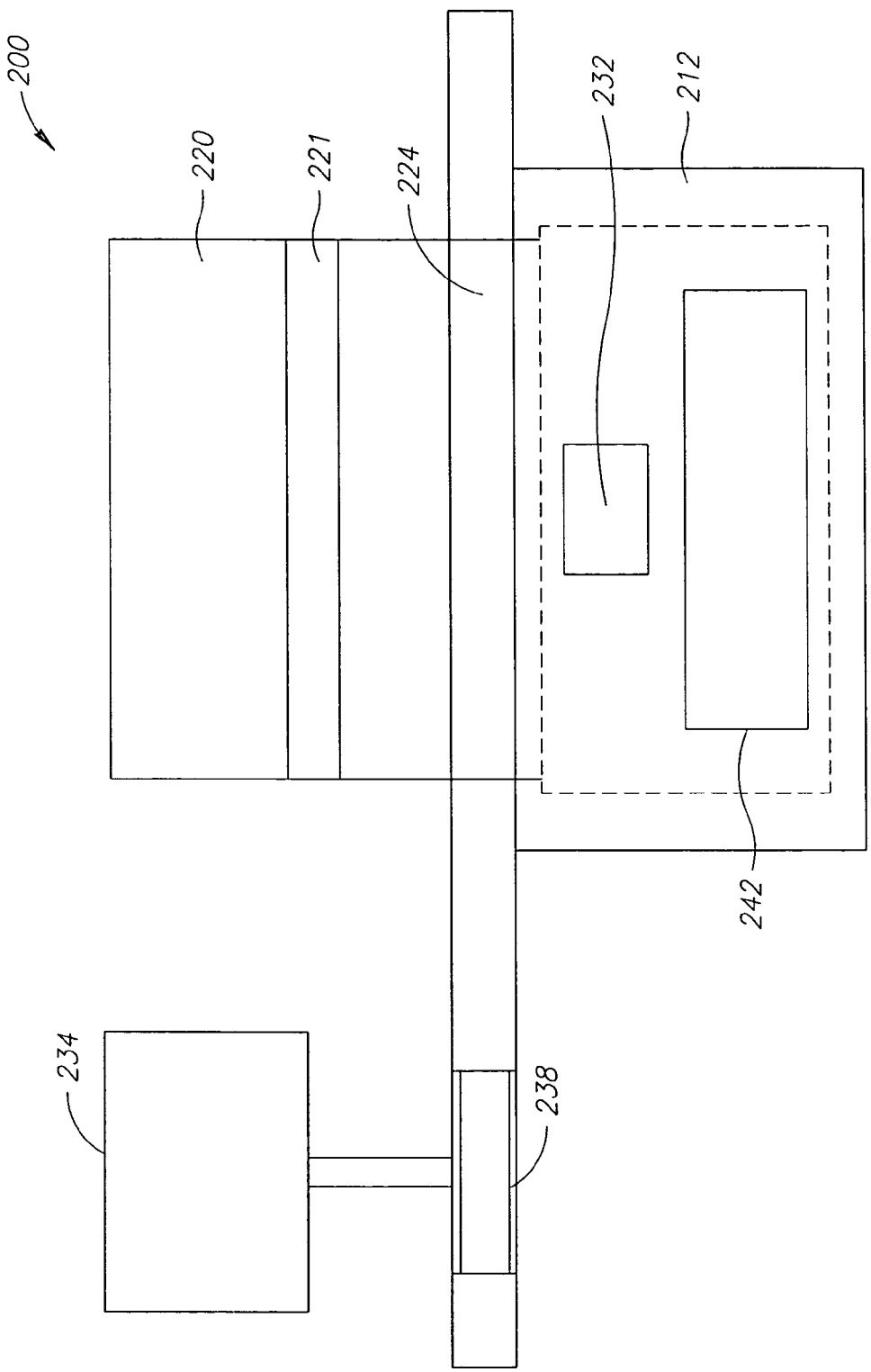
Figure 2D:
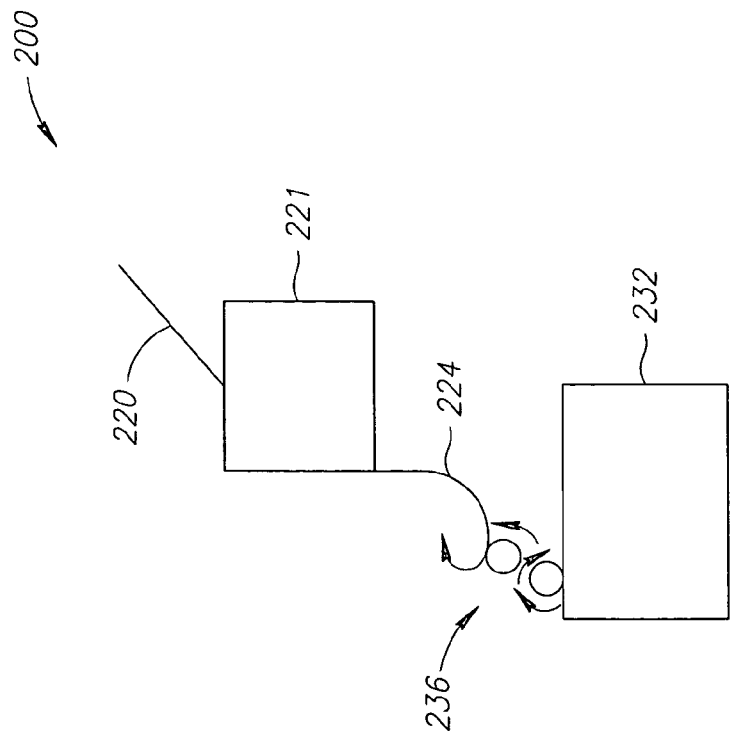
FIG. 2D is a schematic view of the conveyor and conveyance of the printout constructed according to an embodiment of the present invention.
Figure 2C:
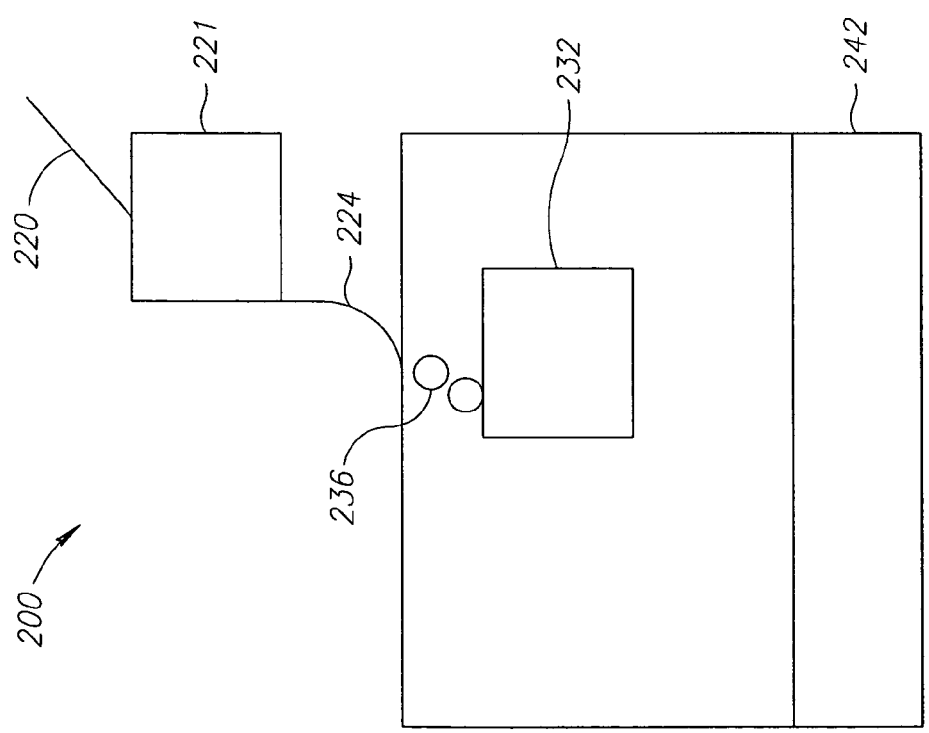

FIGS. 2A-2C, to which reference is now made, show various schematic views of a workstation of the present invention, generally referenced as 200, constructed according to an embodiment of the present invention. FIG. 2A is a full front view, FIG. 2B is a cut-away front view and FIG. 2C is a side view of the workstation. Workstation 200 includes a display 234, a keyboard 238 and a computer processor 242, the latter located within the body 212 of workstation 200. It also may include an input device (not shown), which may be a computer mouse, touch screen or other such devices.

Integrated with body 212 of workstation 200 is a scanner 221 which is in electronic communication with processor 242. A film feed 220 of scanner 221 is shown at the top of workstation 200. Radiological films containing mammogram images are placed in film feed 220 and scanned through scanner 221 from which digitized images are transferred to processor 242 and then displayed on display 234. The scanned films then drop into a collating station 224 of workstation 200. Without being limiting, a scanner that can be used is the Mammography Pro™ scanner produced by Vidar Systems Corporation.

The films of a patient are scanned one after the other by scanner 221 and after each film is scanned they fall onto the previously scanned film already lying in collating station 224. Generally four films of a patient, representing craniocaudal (CC) and mediolateral oblique (MLO) views of each breast, are scanned. Processor 242 receives the scanned digital images from scanner 221 and processes them so that they are all simultaneously displayed on display 234. It should readily be evident to one skilled in the art that in other workstation configurations a plurality of scanned films relating to a single patient can be processed and displayed sequentially one-by-one or in pairs or in a pre-determined manner.

When the four films are displayed together, the films are regularly placed in preselected positions. For example, the upper two pictures on display 234 can be the right and left craniocaudal (CC) views respectively while the bottom two views, the right and left mediolateral oblique (MLO) views, can be lined up directly below the respective CC views. Alternatively, films of the right breast can be displayed above the left breast with the right CC view over the left CC view and the right MLO view over the left MLO view. Other display orders are also possible.

In general an algorithm used by the processor recognizes each of the scanned films as a CC or MLO view. It also recognizes if the film relates to the left or right breast of the patient. After recognition, the processor then displays the views in the pre-selected order on display 234. This automatic sequencing replaces time-consuming sorting by a technician, with a reduction in human error.

Each of the displayed films include location markers circumscribing suspected abnormalities. Processor 242, using any of many algorithms known in the art, determines the existence of abnormalities. Examples of algorithms which can be used are discussed in U.S. Pat. Nos. 5,854,581 and 5,970,164 both to Bamberger et al, and both incorporated herein by reference in their entirety. The radiologist examines the displayed views, particularly the areas marked as suspicious lesions, before making a final diagnosis and/or prescribing a course of action.

Generally, prior to scanning a new set or sets of films, i.e. films relating to one or more patients, the operator, using keyboard 238, enters the one or more patients' identifier data. This typically includes but is not limited to name, age, identifier number, etc. This step obviates the need for using bar codes or adhesive stickers containing identifier data as is currently being done. After the digitized images of the scanned film mammograms of a patient have been stored in processor 242 they can be retrieved at any time by a radiologist for re-viewing by inputting the previously inputted patient identifier data.

Typically, a separator film is placed immediately after a patient's set of film mammograms in film feed 220. The separator film contains a preprinted pattern, graphical indicia, design or other identifier recognizable by the scanner and/or processor as indicating a separator film. In addition, or alternatively to a preprinted pattern, the separator can have a predefined edge, such as a textured or serrated edge, which differs from the edges of the previously scanned set of radiological films. The different shaped edge can be discriminated by the scanner as indicating a separator film.

After the separator film is scanned, processor 242 recognizes that the end of the set of film mammograms relating to patient Jones has been reached and that the next mammogram relates to patient Smith. Processor 242 then automatically instructs printer 232 to print the digitized images of patient Jones displayed on display 234, including the marked suspected abnormalities shown thereon. The printout of the displayed digitized images is then delivered directly and automatically to collating station 224 by a conveyor 236. The conveyor 236 used in FIG. 2C is a system of rollers 236. In collating station 224, the printout falls onto its associated set of film mammograms that have been scanned previously and from which the displayed digitized images have been generated. Finally, the separator film drops from scanner 221 onto collating station 224 where it forms a complete collated package with the film mammograms and associated printout for patient Jones. The procedure is then repeated for patient Smith and all succeeding patients.

It should be noted that the separator film has two functions. It indicates to the processor that the next film to be scanned relates to a different patient and should be associated with different identifier data. Additionally, at a later stage after film/printout collation has been completed at collating station 224, it indicates to the technician filing the radiological films and their associated printout that the collated material for one patient has ended and data for a new patient lies below. Accordingly, the technician knows to file the data between a pair of separator films in a single storage container, generally a physical folder, for storage in the medical records department, the radiology department, or elsewhere.

Processor 242 can be pre-programmed to stop scanner 221 from scanning when it determines that no identifier data has been supplied.

In another embodiment, identifier data could be entered during the process of generating the film mammograms. Such data could be inputted and coded directly and automatically onto the film mammograms as they are being processed. When scanner 221 scans the films, the identifier data can be read and stored in processor 242 with the digitized images.

In yet another embodiment, a set of film mammograms may be scanned by scanner 221, digitized and displayed on display 234. Then using keyboard 238, the radiologist or technician instructs printer 232, which is in communication with processor 242, to print the digitized images displayed on display 234, including the marked suspected abnormalities shown thereon. The displayed image printout is then delivered directly and automatically to collating station 224 by a conveyor 236. The conveyor used in FIG. 2C is primarily a system of rollers 226. In collating station 224, the printout falls onto its associated set of films that have been previously scanned and from which the displayed digitized images have been generated. After the printout of the digitized images has automatically been placed on the set of scanned films, a separator film is inserted into film feed 220 and scanned. The processor detects the separator film and knows that any subsequent film mammograms belong to another patient. The separator then drops onto the film mammograms and printout lying in collating station 224.

While the separator film that has been discussed above, and will be discussed below, has been described in terms of radiological films having predetermined designs or patterns or films having distinctive edges, separators with other distinguishing features or marks may also be used.

It should be noted that for purposes of simplicity, processor 242 has been shown in FIGS. 2B-2C (and below in FIGS. 3A-3B), and described in conjunction therewith, as a single unit. In reality it represents a complete "processing means" that includes both hardware and software systems which are in electronic communication with scanner 221, printer 232, and display 234, coordinating their activities. Processor 242 also includes a "means for synchronizing" which synchronizes the scanning done by scanner 221 and printing done by printer 232. Processor 242 also contains a memory for storing digitized images and patient input data, the latter provided inter alia by an input device such as keyboard 238. In what is described herein, including in the claims, "processor" and "processing means" will be used synonymously without any intent at distinguishing between them.

FIG. 2D to which reference is now made shows in a schematic fashion the conveyance of the printout from printer 232 over a series of rollers 236 into collating station 224 where rollers 236 serve as the conveyor 236 of the printout.

Figure 3A:
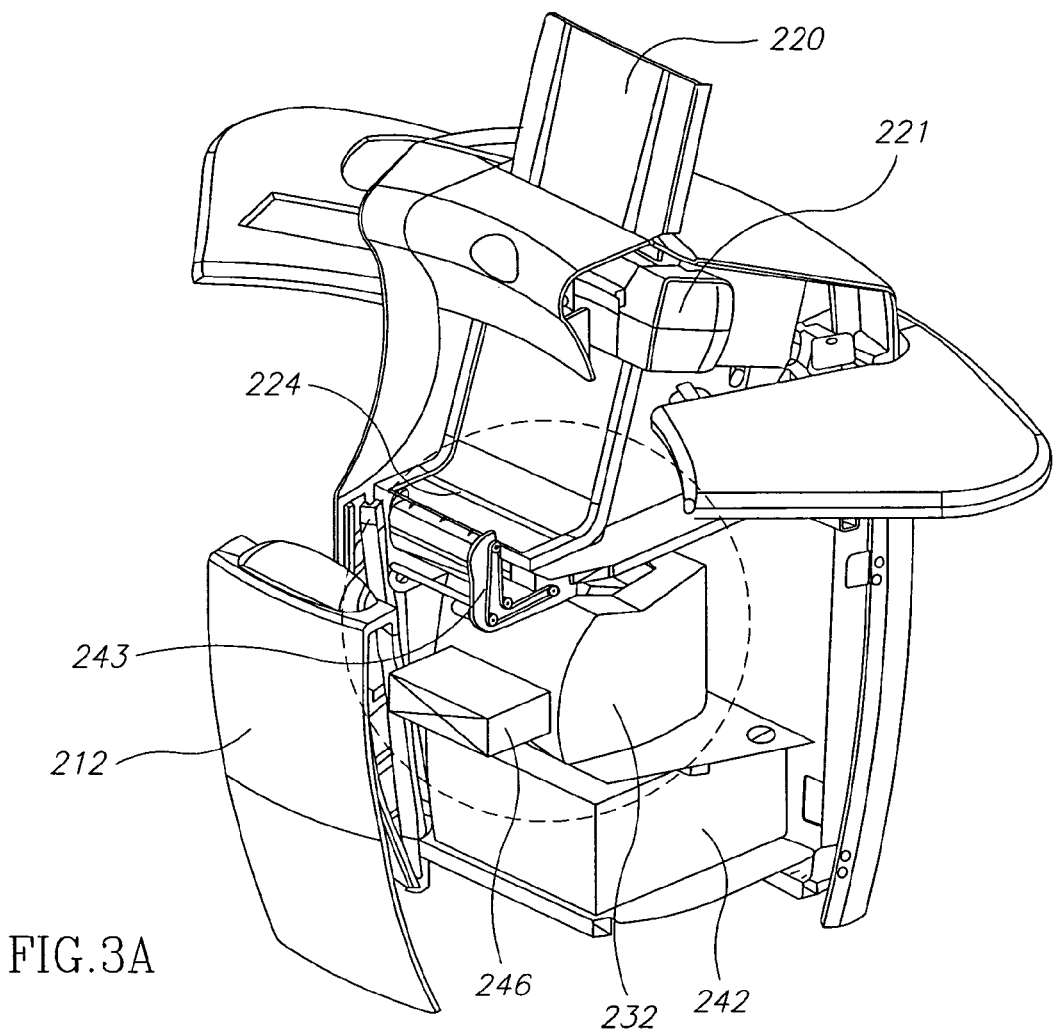
FIGS. 3A-3B are isometric cut-away and enlarged cut-away views respectively of a body of a workstation constructed in accordance with another embodiment of the present invention.
Figure 3B:
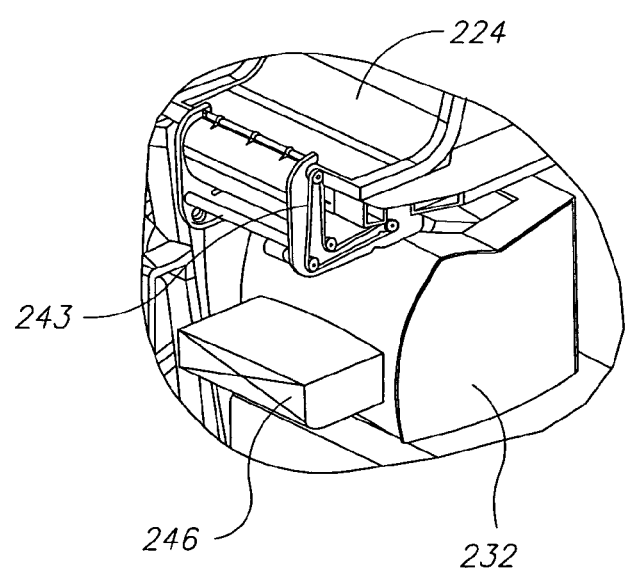

Reference is now made to FIG. 3A which shows an isometric view of workstation 200 with a cut-away view of its body 212 and FIG. 3B which shows an expanded view of printer 232, conveyor 236, which here is a simple paper guide 243, and collating station 224.

FIG. 3A shows printer 232, including paper station 246, which generates a printout of the scanned digitized images. Paper guide 243 guides the printout from printer 232 to collating station 224. FIG. 3B shows an expanded isometric view of printer 232, paper guide 243, and collating station 224. Paper guide 243 acts as a conveyor 236 just as roller 236 does in FIGS. 2C and 2D. It should be evident that constructions other than rollers 236 shown in FIGS. 2C and 2D and paper guide 243 shown in FIGS. 3A and 3B can also serve as a conveyor of the printout from printer 232 to collating station 224. For example, and without being limiting, the many different types of paper conveyor systems in photocopier machines can be adapted for use in workstation 200.

Reference is now made to FIGS. 4A-4D, where several embodiments of the method of the present invention are illustrated.

Figures 4A, 4B:
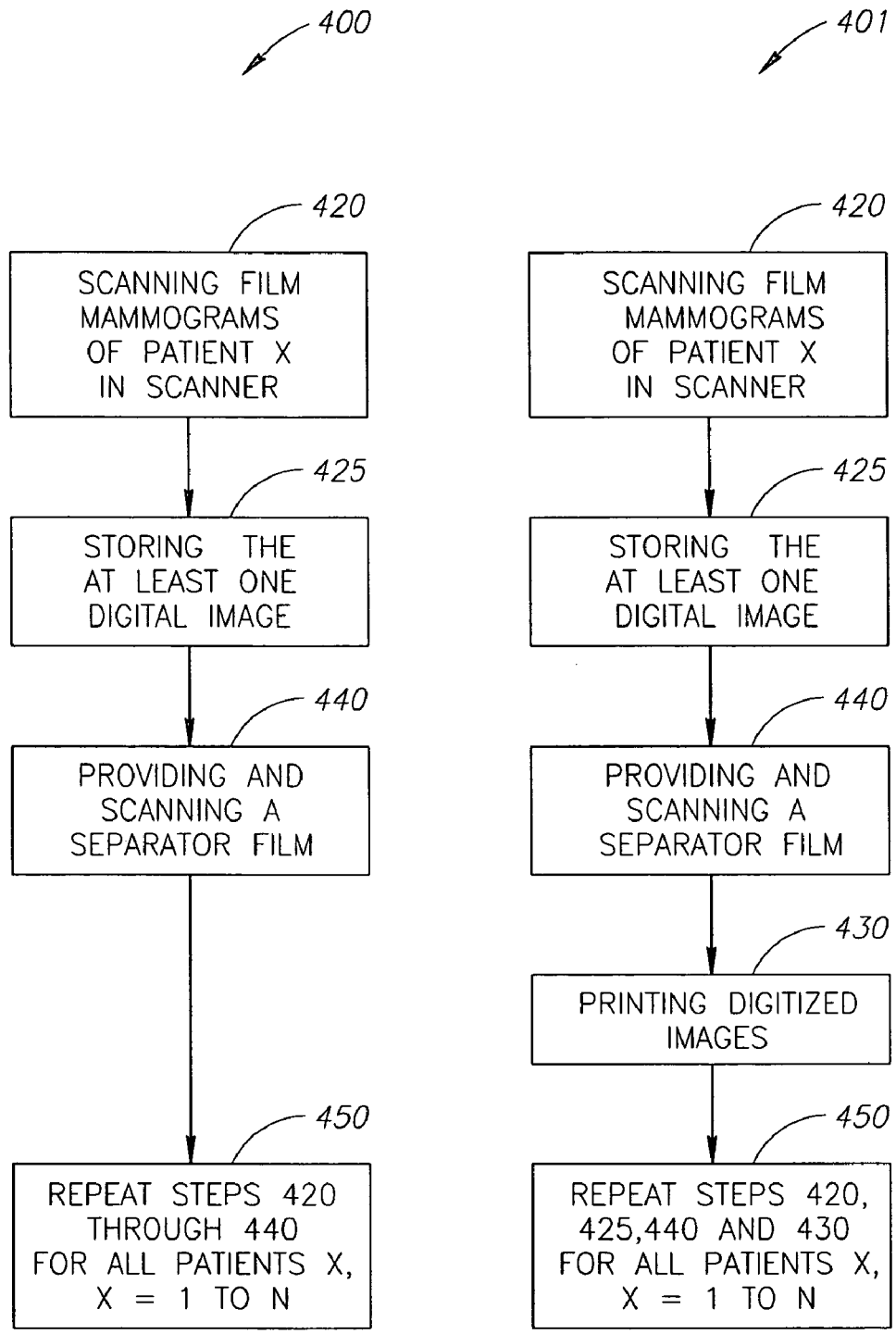
FIGS. 4A-4D show flow charts of four embodiments of the method of the present invention.

In FIG. 4A, a flowchart is presented where the method is generally referenced 400. A set of radiological films, usually four films including a craniocaudal (CC) and a mediolateral oblique (MLO) view of each breast of a patient, patient X, are scanned (step 420) by a mammogram scanner. The scanned analog film mammograms are converted into digitized images. The scanned digitized film images are delivered to the processor of the workstation where they are stored (step 425) in memory. The scanned films then drop into a collating station of the workstation.

A technician then provides a separator film to the scanner in providing step 440. The separator film contains a preprinted pattern, design or other identifier recognizable by the scanner and/or processor as indicating a separator film. In addition, or alternatively to a preprinted pattern, the separator can have a predefined edge, such as a textured or serrated edge, which differs from the edges of the previously scanned set of radiological films. The different shaped edge can be discriminated by the scanner as indicating a separator film. After being scanned the separator film falls into the collating station on top of the original mammogram films. In practice, in providing step 440, a separator film generally is placed simultaneously in the film feed of the scanner and positioned as the last film in a set of one or more radiological films relating to patient X.

In repeating step 450, scanning step 420, storing step 425 and providing step 440 are repeated for as many sets of patient film mammograms as desired. The sets of films inputted forms a queue of mammograms for N, where $N \geq 1$, patients which are to be reviewed by a radiologist.

Generally, several sets of radiological films are placed in the workstation film feed simultaneously, each set separated from subsequent sets by a separator film. A set of mammogram films consists of one or more films. Each set relates to a different patient and is recognized as such by the processor when a separator film is detected.

Practically, the film feed of the scanner limits the number of sets of films that can be inputted serially at one time. The flowchart of FIG. 4A indicates that the maximum number of patients for which films may be scanned and collated as N. In theory, method 400 allows for collation of an unlimited number of mammograms.

All digitized images generated after a scanned separator film has been recognized are stored separately from all prior digital images stored in storing step 425. In effect when the entire film mammogram queue is stored the digitized images of each patient are stored separately from all of the other patients.

In FIG. 4B a flowchart is presented showing another embodiment of the method of the invention. In FIG. 4B the method is generally referenced as 401 and is very similar to the one shown in FIG. 4A. A set of radiological films, usually four films of a patient, patient X, is placed in the film feed of a mammogram scanner and scanned (step 420). The scanner converts the analog film images to digitized images. The digitized images generated by the scanner are fed into the processor of the workstation and stored (step 425). The scanned films then drop into a collating station of the workstation.

A technician then provides a separator film to the scanner in providing step 440. As in the embodiment discussed in conjunction with FIG. 4A, the separator film contains a preprinted pattern, design or other identifier recognizable by the scanner and/or processor as indicating a separator film. In addition, or alternatively to a preprinted pattern, the separator can have a defined edge different from the edges of the previously scanned set of radiological films. In practice, in providing step 440, a separator film generally is placed simultaneously in the scanner and positioned as the last film in a set of one or more radiological films relating to patient X.

When the processor recognizes that a separator film is or has been scanned, a printing step 430 is automatically initiated. In printing step 430, a printer produces a printout on at least one sheet of paper of the digitized images of the scanned radiological films together with any processor-detected abnormalities. Scannable identifier data associated with the original radiological films may also be included on the sheet. The sheet is conveyed automatically to the collating station and placed on top of the scanned radiological films. The scanned separator film then drops from the scanner to the collating station on top of the collated printout and radiological films relating to a single patient, patient X.

In repeating step 450, scanning step 420, storing step 425, providing step 440 and printing step 430 are repeated for as many sets of patient film mammograms as desired. The sets of films inputted forms a queue of film mammograms relating to N patients which are to be reviewed by a radiologist.

Generally, several sets of radiological films are placed in the workstation film feed simultaneously, each set separated from subsequent sets by a separator film. A set of mammogram films consists of one or more films. Each set relates to a different patient and is recognized as such by the processor of the workstation when a separator film is detected.

The flowchart of FIG. 4B indicates the maximum number of patients for which films may be scanned and collated as N, where $N \geq 1$. In theory, however, the number is not limited.

All digitized images generated after a scanned separator film has been recognized are stored separately from all prior digital images stored in storing step 425. As in FIG. 4A above (and FIGS. 4C and 4D to be discussed below), in effect when the entire film mammogram queue is stored the digitized images of each patient are stored separately from all of the other patients.

Figures 4C, 4D:
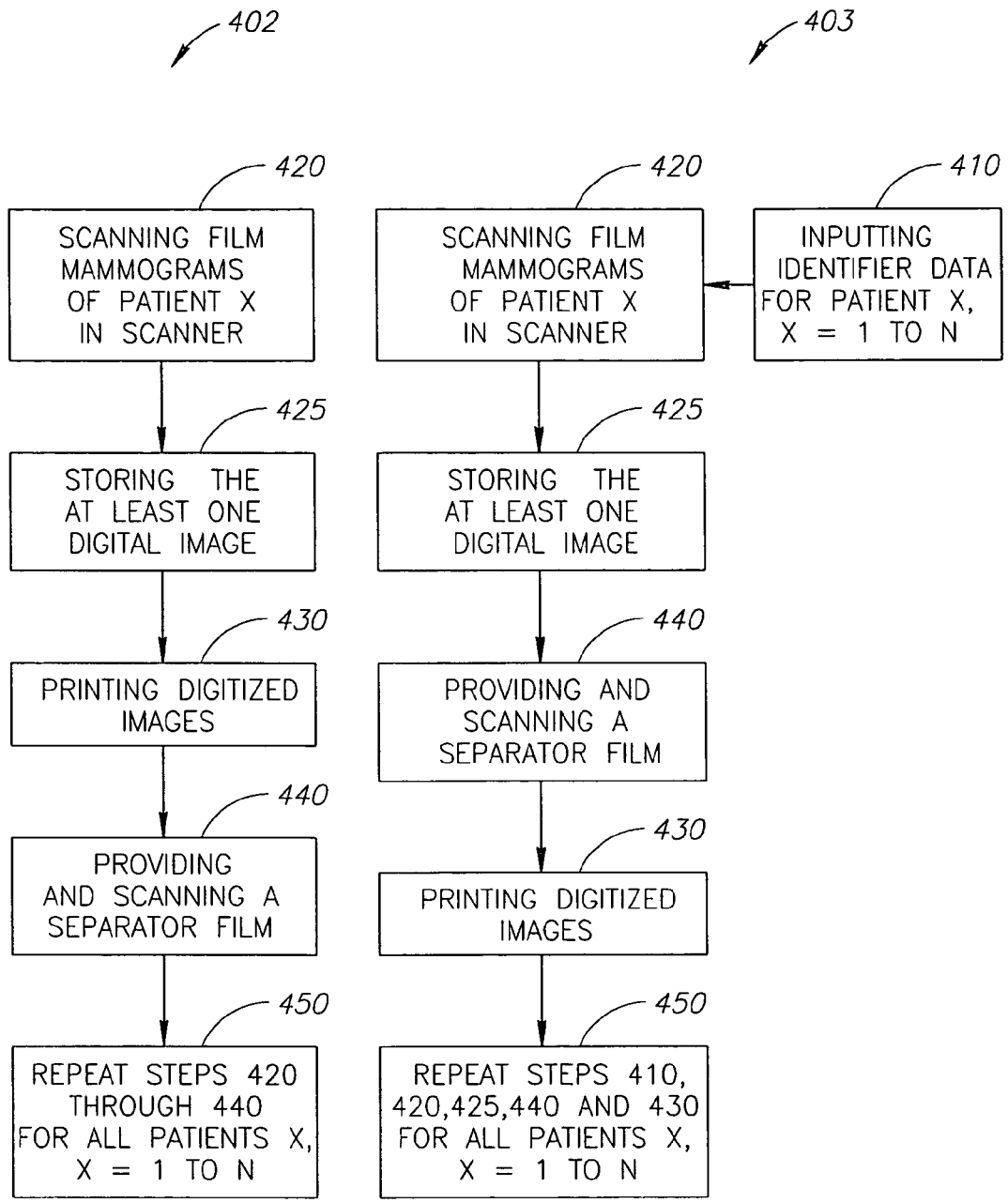

In FIG. 4C a flowchart is presented showing another embodiment of the method of the invention. In FIG. 4C the method is generally referenced as 402 and is very similar to the one shown in FIGS. 4A-4B. A set of radiological films, usually four films, is placed in the film feed of a mammogram scanner which scans (step 420) the analog film mammograms and converts them to digitized images. The digitized images generated by the scanner are fed into the processor of the workstation and stored (step 425) in memory. The scanned films then drop into a collating station of the workstation.

The operator then initiates a printing step 430 in which the scanned films together with any processor detected abnormalities are printed on at least one sheet of paper. Scannable identifier data associated with the original radiological films may also be included on the sheet. The sheet is conveyed automatically to the collating station of the scanner and placed on top of the scanned radiological films.

A technician then provides a separator film into the film feed in providing step 440. As in the embodiments discussed in conjunction with FIGS. 4A-4B, the separator film contains a preprinted pattern, design or other identifier recognizable by the scanner and/or processor as indicating a separator film. In addition, or alternatively to a preprinted pattern, the separator can have a defined edge different from the edges of the previously scanned set of radiological films. After being scanned the separator film falls into the collating station of the scanner on top of the one or more printout sheets and the original mammogram films.

In repeating step 450, scanning step 420, storing step 425, printing step 430 and providing step 440 are repeated for as many sets of patient film mammograms as desired. The sets of films inputted forms a queue of film mammograms for N patients which are to be reviewed by a radiologist. The flowchart of FIG. 4C indicates the maximum number of patients for which films may be scanned and collated as N, where N≧1. In theory, however, the number is not limited.

All digitized images generated after a scanned separator film has been recognized are stored separately from all prior digital images stored in storing step 425. In effect when the entire film mammogram queue is stored the digitized images of each patient are stored separately from all of the other patients.

In FIG. 4D a flowchart is presented showing another embodiment of the method of the invention. In FIG. 4D the method is generally referenced as 403 and is very similar to the one shown in FIG. 4B.

An operator of the workstation first inputs 410 patient identifier data into the processor, typically by using a keyboard. The identifier data includes name, age, identifying number etc. and is stored in the processor of the workstation.

A set of radiological films, usually four films, is placed in the film feed of a mammogram scanner and scanned (step 420). The scanner converts the analog mammogram films to digitized images. The digitized images are fed into the processor of the workstation where they are stored (step 425) in memory. The scanned films then drop into a collating station of the workstation. The stored digitized images provided by the scanner are associated with the identifier data inputted in input step 410.

A technician then provides a separator film to the scanner in providing step 440. As in the embodiment discussed in conjunction with FIG. 4A, the separator film contains a preprinted pattern, design or other identifier recognizable by the scanner and/or processor as indicating a separator film. In addition, or alternatively to a preprinted pattern, the separator can have a defined edge different from the edges of the previously scanned set of radiological films. In practice, in providing step 440, a separator film generally is placed simultaneously in the scanner and positioned as the last film in a set of one or more radiological films relating to a single patient.

When the processor recognizes that a separator film is or has been scanned, a printing step 430 is automatically initiated. In printing step 430, a printer produces a printout of the digitized images of the scanned radiological films together with any processor detected abnormalities on at least one sheet of paper. The printout also includes identifier data entered in step 410 and stored in the processor as described above. The sheet is conveyed automatically to the collating station and placed on top of the scanned radiological films. The scanned separator film then drops from the scanner to the collating station on top of the collated printout and radiological films relating to a single patient.

Similar to the methods discussed in conjunction with FIGS. 4A-4C, in repeating step 450, inputting step 410, placing step 420, storing step 425, separating step 440, and printing step 430 are repeated for as many patients as desired. The number of films inputted forms a queue of patients for review by the radiologist.

All digitized images generated after a scanned separator film has been recognized are stored separately from all prior digital images stored in storing step 425. In effect when the entire film mammogram queue is stored the digitized images of each patient are stored separately from all of the other patients.

In another embodiment similar to the one shown and discussed in conjunction with FIG. 4D, inputting step 410 is not repeated in repeating step 450. Instead inputting step 410 consists of inputting identifier data for all of the patients having a set of mammograms in the film mammogram queue before any scanning of the sets of mammograms begins. This obviates the need for repeating inputting step 410 in repeating step 450.

The embodiment discussed in conjunction with FIG. 4D is essentially the same as the embodiment shown and discussed with FIG. 4B except for the addition of an inputting step. It should readily be understood by one skilled in the art that an inputting step can also be added to the embodiments shown in and discussed with FIGS. 4A and 4C.

In the above description of the method, the internal separation aspect, that is the processor separation aspect, of the invention has been emphasized. The digitized images of the different sets of film mammograms are stored separately in the memory of the processor. In another aspect of the invention already mentioned above, the present invention allows for the collation of physical data and facilitates filing and storage of the physical records generated in mammogram screening.

Embodiments of this collating aspect of the invention include the following steps, which, as can readily be seen, are essentially the same as those discussed in conjunction with the embodiments of FIGS. 4A-4D. However, this aspect of the invention makes no mention of the processor digitized image storage aspect of the invention and relates solely to the physical records, the film mammograms and printout, of individual patients.

The steps include:
1. Scanning a set of radiological film mammograms of a patient, patient X, using a mammogram scanner.
2. Moving the scanned set of film mammograms to a collating station of the workstation.
3. Providing and scanning a separator film.
4. Positioning the separator film on top of the scanned set of film mammograms in the collating station.
5. Repeating the scanning, moving, providing and positioning steps for each of the N sets of patient film mammograms to be scanned. The N inputted sets of films inputted forms a queue of film mammograms for N patients, where N≧1, which are to be reviewed by a radiologist.
6. Transferring the collated packages of each of the N sets of film mammograms positioned between separator films to their N individual storage containers for storage.

Generally, several sets of radiological films are placed in the workstation film feed simultaneously, each set separated from subsequent sets by a separator film. As mentioned previously, a set of mammogram films consists of one or more films. Each set relates to a different patient and is recognized as such by the processor when a separator film is detected.

In effect, all scanned film mammograms dropping onto a scanned separator film and then covered by another scanned separator film are recognized as relating to a single patient. When the entire film mammogram queue is scanned the film mammograms positioned between two separators are filed separately from the other sets of film mammograms in their individual storage containers.

In addition to the above steps, other steps, taken singly or together, may be used with the above steps.

When the processor recognizes that a separator film is, or has been, scanned, a printing step may be automatically initiated. In the printing step, a printer produces a printout on at least one sheet of paper of the digitized images of the scanned radiological films of patient X, where X is patient 1 to N. the printout also includes any processor-detected abnormalities. Scannable identifier data associated with the original radiological films may also be included on the sheet. In a conveying step, the printout is conveyed automatically to the collating station and placed on top of the scanned radiological films. The scanned separator film then drops from the scanner onto the collating station on top of the collated printout and radiological films which together form a collated set of physical data relating to a single patient, patient X.

The method may also include an inputting step. An operator of the workstation may initiate an input step by inputting identifier data into the processor, typically by using a keyboard. The identifier data includes name, age, identifying number etc. and is stored in the processor of the workstation.

The printing step can be effected both prior to the providing step or prior to the positioning step. When a printing step is used it is generally included in the repeating step.

Similarly when their is an inputting step the inputting step can be effected prior to the providing step but more often prior to the scanning step. When an inputting step is used it is generally included in the repeating step.

In another embodiment, the inputting step is not repeated in the repeating step. Instead the inputting step consists of inputting identifier data for all of the patients having a set of mammograms in the film mammogram queue before any scanning of the sets begins. This obviates the need for repeating the inputting step in repeating step.

In other embodiments of the method, there is an additional step that is not indicated in the flowcharts of FIGS. 4A-4D. It serves as the final step of the embodiment of the methods discussed in conjunction with FIGS. 4A-4D. After the radiological films and printout are collated and separated between two separator films, a technician files the scanned radiological films and their associated printout in a single physical storage container. Only collated films and printouts located between two nearest separator films are filed in a single physical storage container. The storage container is typically, but not necessarily, a medical records or radiology department folder.

Whenever a radiologist wishes to review a patient's records he can review the contents of the patient's physical storage container, which contains the radiological films and display printout of the patient. Alternatively, he may return to the list of patients whose scanned digitized film mammograms are stored in the system's processor and which can be viewed on the system's display. The radiologist indicates on the display, typically by using a computer mouse or keyboard, the patient for which he wishes to review the stored, scanned images.

It should readily be evident to one skilled in the art that in addition to identifier data the printout may contain diagnostic data provided by the processor's algorithm. This may include, but is not limited to, an overall evaluation of the likelihood of malignancy determined by the algorithm used by the processor.

It will be appreciated by persons skilled in the art that the present invention is not limited by what has been particularly shown and described hereinabove. Rather the scope of the invention is defined by the claims that follow.

What is claimed is:

1. A method of separating and collating mammogram records, said method including the steps of:

inputting patient identification data for a series of N patients, where N≧1, using an inputting device, the identification data stored in a memory of a processor;

scanning at least one radiological film mammogram relating to a patient thereby to obtain at least one digitized image of the at least one film mammogram;

storing the at least one digitized image in the memory of the processor;

providing and scanning a separator film having identifiable features which when scanned identify the film as a separator film, and positioning the separator film immediately after the at least one radiological film of the patient; and repeating said steps of scanning, storing, and providing for the remaining film mammograms for the N patients in a film mammogram queue;

wherein the separator films allow for associating the at least one film mammogram between each of two nearest separator films in sequential fashion with the inputted identification data of the series of N patients.

2. A method according to claim 1 further including a step of printing a printout of the at least one digitized image of the at least one film mammogram of the patient, and further including a step of conveying the printout from the printer, so that the printout falls onto its associated at least one film mammogram, the printout and the associated at least one film mammogram forming a collated package of physical data related to the patient, said steps of printing and conveying being synchronized so as to allow for collation of the printout with its associated at least one film mammogram in the collated package of physical data.

3. A method according to claim 2 wherein said step of printing provides a printout which contains location markers indicating anatomical abnormalities detected by the processor on a mammogram.

4. A method according to claim 2 wherein said step of printing a printout is effected prior to said step of providing and scanning.

5. A method according to claim 2 wherein said step of printing a printout is effected after said scanning of a separator film in said step of providing and scanning.

6. A method according to claim 2 wherein said step of repeating also includes repeating said step of printing.

7. A method for separating and collating mammogram records, said method including the steps of:

inputting patient identification data for a series of N patients where N≧1 using an inputting device, the identification data stored in a memory of a processor;

scanning a set of film mammograms relating to a patient thereby to obtain at least one digitized image of the set of film mammograms;

moving the scanned set of film mammograms to a collating station;

providing and scanning a separator film having identifiable features which when scanned identify the film as a separator film, and positioning the separator film immediately after the set of film mammograms of the patient so that the separator film functions as the last film of the scanned set of film mammograms of the patient located at the collating station and allows for associating the set of film mammograms between each of two nearest separator films in sequential fashion with the inputted identification data of the series of N patients;

repeating said steps of scanning, moving, and providing for the N sets of film mammograms in a film mammogram queue; and transferring each of the N sets of film mammograms positioned between two nearest separator films to its own individual physical storage container for storage.

8. A method according to claim 7 further including:
a step of printing to provide a printout of the at least one digitized image of the set of film mammograms; and
a step of conveying wherein the printout is conveyed to, falls on and is positioned together with its associated set of film mammograms of the patient at the collating station,
whereby the set of film mammograms and printout together form a collated package of physical data relating to the patient, said steps of printing and conveying being synchronized so as to allow for collation of the printout with its associated set of film mammograms in the collated package of physical data.

9. A method according to claim 8 wherein said step of printing provides a printout which contains location markers indicating anatomical abnormalities detected by the processor on a mammogram.

10. A method according to claim 8 wherein said steps of printing and conveying are effected prior to said step of providing.

11. A method according to claim 8 wherein said steps of printing and conveying are effected prior to said step of positioning.

12. A method according to claim 8 wherein said step of repeating also includes repeating said steps of printing and conveying.

13. A workstation system for collating radiological film mammograms and other physical records, said system including:
a scanner operative to receive and digitize radiological film mammograms from a patient and a separator film carrying identifiable features for identifying the film as a separator film;
a collating station for receiving the scanned films from said scanner;
processing means for receiving digitized images from said scanner operative to evaluate the digitized images of the film mammograms so as to detect suspicious lesions therein, further operative to generate output data indicative thereof and to store the data in association with the digitized images;
wherein said processing means is further operative to detect said scanned separator film and to assign all subsequent scanned radiographic film mammograms to other patients;
a printer in communication with said processing means for producing a printout of the digitized images identifying data and output data relating to the patient, said printer including a conveyor for conveying the printout to said collating station; and
means for synchronizing said scanner and said printer such that the printout of the scanned films of a patient is laid on the scanned film mammograms prior to the delivery to said collating station of said separator film.

14. A system according to claim 13 further including a display for displaying the digitized images of scanned radiological film mammograms received from said processing means which is in electronic communication with said display.

15. A system according to any one of claims 13-14 further including an input device for entering identifier data relating to the patient.

16. A system according to claim 13 wherein the conveyor includes a set of rollers.

17. A system according to claim 13 wherein the conveyor is a paper guide.

* * * * *